(12) United States Patent
Kim

(10) Patent No.: US 6,986,777 B2
(45) Date of Patent: Jan. 17, 2006

(54) AUTOMATIC LANCING DEVICE

(76) Inventor: Yong Pil Kim, #103-601 Daelimgyoungdong Apt., 1474 Gayang-dong, Gangseo-gu, Seoul 157-200 (KR)

( * ) Notice: Subject to any disclaimer, the term of this patent is extended or adjusted under 35 U.S.C. 154(b) by 485 days.

(21) Appl. No.: 10/251,622

(22) Filed: Sep. 20, 2002

(65) Prior Publication Data

US 2003/0199892 A1   Oct. 23, 2003

(30) Foreign Application Priority Data

Apr. 22, 2002   (KR) ............................ 2002-12172 U

(51) Int. Cl.
  *A61B 17/34*   (2006.01)
(52) U.S. Cl. ..................................................... 606/182
(58) Field of Classification Search ................ 606/182, 606/183; 600/583
  See application file for complete search history.

(56) References Cited

U.S. PATENT DOCUMENTS

| 4,203,446 | A | * | 5/1980 | Hofert et al. ................ 606/182 |
| 4,462,405 | A | * | 7/1984 | Ehrlich ........................ 606/182 |
| 4,469,110 | A | * | 9/1984 | Slama ......................... 600/583 |
| 4,527,561 | A | * | 7/1985 | Burns ......................... 606/182 |
| 5,074,872 | A | * | 12/1991 | Brown et al. ................ 606/182 |
| 5,350,392 | A | * | 9/1994 | Purcell et al. ............... 606/182 |
| 5,628,764 | A | * | 5/1997 | Schraga ...................... 606/182 |
| 6,045,567 | A | * | 4/2000 | Taylor et al. ................ 606/181 |

* cited by examiner

*Primary Examiner*—Michael Thaler
(74) *Attorney, Agent, or Firm*—Merchant & Gould P.C.

(57) ABSTRACT

The present invention generally relates to an automatic lancing device for withdrawing a blood sample, comprising a pushing member positioned at a back end of a body and a rotatable cap combined with a front end of the body for regulating the combination length of the body and the ejection length of a lancet, thereby obtaining a blood sample exactly at a desired position without misoperation and adjusting the penetration length of lancet according to depth of the skin.

2 Claims, 5 Drawing Sheets

(a)

(b)

(c)

AUTOMATIC LANCING DEVICE

BACKGROUND OF THE INVENTION

1. Field of the Invention

The present invention generally relates to a lancing device for withdrawing a blood sample for medical treatment, and more particularly, to an automatic lancing device obtaining a blood sample exactly at a desired position without misoperation and adjusting the penetration length of lancet according to depth of the skin.

2. Description of the Prior Art

Generally, a lancing device is used when a small amount of blood is needed in medical treatment procedures, such as blood type test or blood sugar test.

In the conventional lancing device, as shown in FIG. 5, a lancet (not shown) receiving an elasticity generated by an elastic member, such as spring (not shown), is mounted within a case 50. The lancet is automatically ejected from the front end of the case 50 by means of elasticity of the elastic member, thereby piercing the skin at a predetermined depth. The lancing device elongates the elastic member positioned at the inside of the case 50 by moving an operating member 52 positioned at a back end of the case 50 to the rear. A pushing member 51 is formed to protrude from one side of the case 50. When the protruded pushing member is pushed, the spring is contracted and generates the elasticity. By means of the said elasticity, The lancet is ejected from the front of the case, thereby piercing the skin. After the lancet pierces the skin, the elastic member retracts the lancet to a safe position within the lancing device.

However, the ejection length of the lancet in conventional the lancing device cannot be regulated. As a result, in order to obtain blood sample at the skin having different depth, a lancing device comprising a lancet having a different ejection length should be used. Furthermore, because the pushing member 51 generating instant impact to the lancet is located at one side of the case 50, a user happens to push the pushing member 51 by mistake when seizing the case 50, thereby piercing an undesired place of the skin.

SUMMARY OF THE INVENTION

Accordingly, an object of the present invention is provide an automatic lancing device that can obtain a blood sample exactly at a desired place by disposing a pushing member at a back end of a body, and regulate the ejection length of the lancet from body corresponding to depth of the skin. In order to achieve the above-described object, An automatic lancing device for withdrawing a blood sample, comprising: a hollow cylindrical body; an operation mechanism having a lancet exchangeably fitted at the front of a lancet holder positioned inside the body, and an impact-receiving member combined with the other side of the lancet holder and receiving impact to eject the lancet from the body; an impact-generating mechanism having an impact-transmitting member positioned at a back end of the operation mechanism and transmitting impact to the impact-receiving member; and a length-regulating mechanism comprising a length-regulating member rotationably combined with the outer circumference of a front case enclosing the lancet at the front end of the body and regulating a ejection length of the lancet from the front case.

The automatic lancing device according to the present invention is characterized in that the impact-generating mechanism comprises: a pushing member being positioned at the back end of the body and having pin-operating holes which penetrate across it; an impact-transmitting member having a penetrating hole and inner-inserted into inside the pushing member, wherein a first elastic member is also inner-inserted inside the pushing member and interposed between the impact-transmitting member and the pushing member; a pin guide member having pin guide holes penetrating across it and outer-inserted into outside the pushing member, wherein a second elastic member is also outer-inserted outside the pushing member and interposed between the pin guide member and the pushing member; and an operating pin passing through the penetrating hole of the impact-transmitting member, the pin-operating hole of the pushing member and the pin-guide hole of the pin guide member and connecting these members.

The automatic lancing device according to the present invention is characterized in that: wherein each of pin guide holes has a circumferential path and an longitudinal path; the operating pin located at the circumferential path is moved into the longitudinal path by the pin-operating hole when the pushing member is pushed; and the impact-transmitting member is moved forward with the operating pin according to the longitudinal path due to the first elastic member storing elasticity while the operating pin is being moved, and transmits impact into the impact-receiving member.

The automatic lancing device according to the present invention is characterized in that the length-regulating mechanism comprises a front case having a helical thread at the outer circumference and the length-regulating member has a protruding portion for moving according to the helical thread.

BRIEF DESCRIPTION OF THE DRAWINGS

The present invention will be explained in terms of exemplary embodiments described in detail with reference to the accompanying drawings, which are given only by way of illustration and thus are not limitative of the present invention, wherein.

DETAILED DESCRIPTION OF THE PREFERRED EMBODIMENTS

Figure 1:
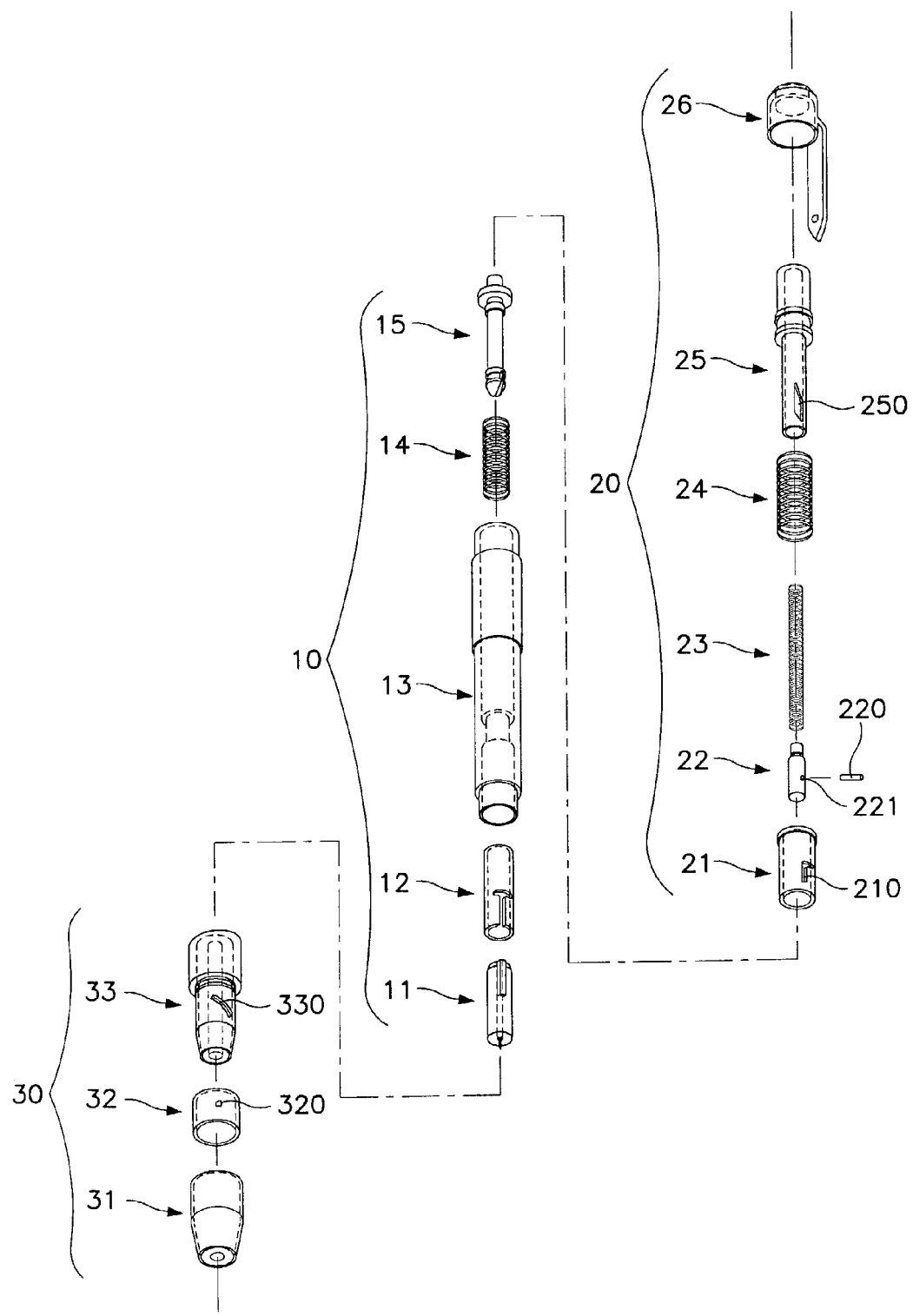
FIG. 1 is an exploded perspective view of an automatic lancing device according to the present invention.

Referring to FIG. 1, an automatic lancing device according to the present invention broadly comprises a hollow cylindrical body 13, an operation mechanism 10 ejecting a lancet 11 instantly to the fore of the body 13 and piercing the skin, an impact-generating mechanism 20 positioned at the back of the operation mechanism 10 and generating instant impact triggering the operation mechanism 10, and a length-regulating mechanism 30 positioned at the front end of the operation mechanism 10 and regulating the ejection length of the lancet 11.

Figure 2:
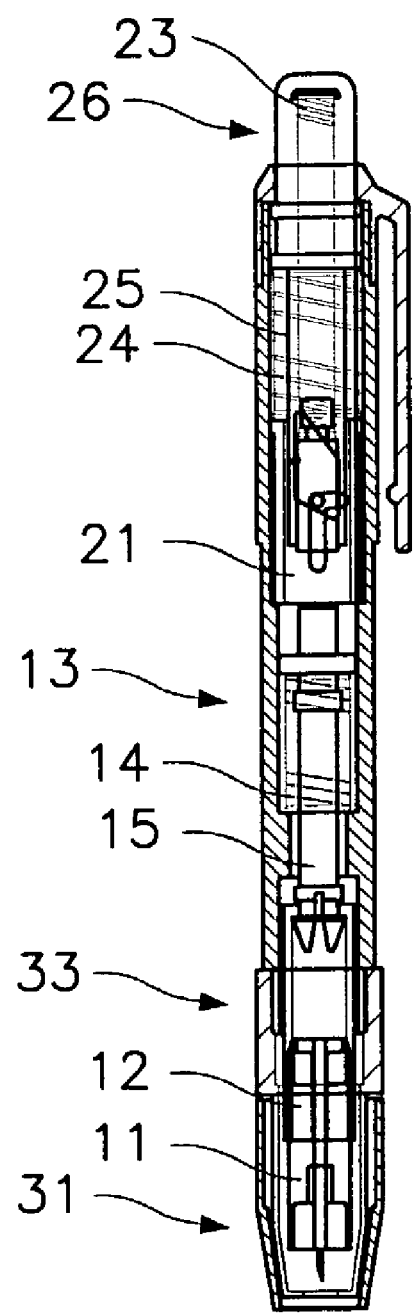
FIG. 2 is a cross-sectional view of an automatic lancing device according to the present invention.

As shown in FIGS. 1 and 2, an operation mechanism 10 has a lancet holder 12 that is inserted into the hollow cylindrical body 13 and a lancet 11 exchangeably fitted at the front of the lancet holder 12. An impact-receiving member 15 is inserted into a return elastic member 14 positioned in the inside of the body 13. The front end of the impact-receiving member 15 is combined with the lancet holder 12. When instant impact generated in the impact-generating mechanism 20 is transmitted into the impact-receiving member 15, the impact-receiving member 15 is moved forwardly. As a result, the lancet 11 connected to the impact-receiving member 15 by way of the lancet holder 12 is moved forwardly. At this time, the return elastic member 14 is contracted with accumulating elasticity, and then instantly is bounced backward. As a result, the lancet 11 instantly pierces the skin and then is retracted.

Figure 3:
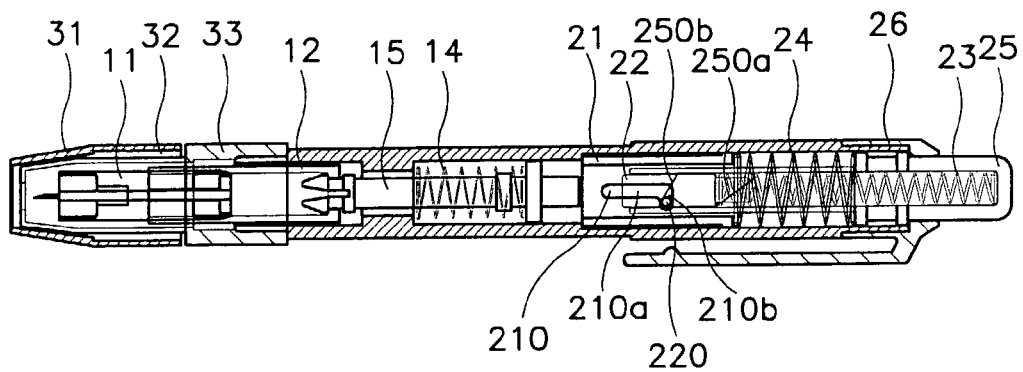
FIG. 3 is an operation state view of an automatic lancing device according to the present invention.
Figure 3:
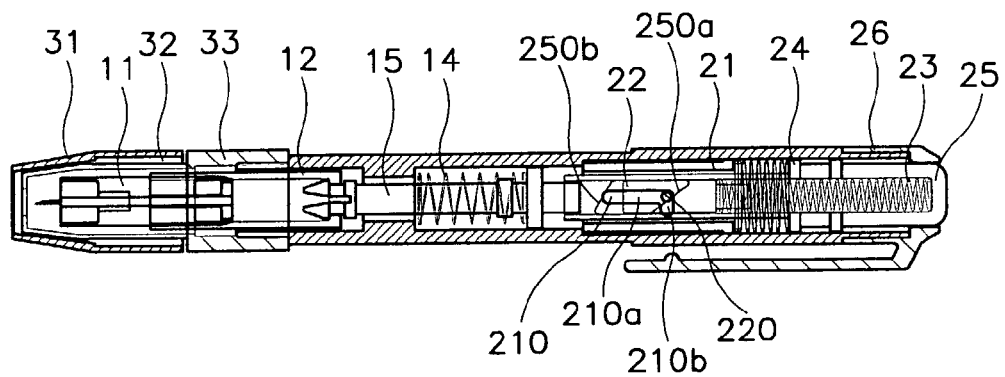
Figure 3:
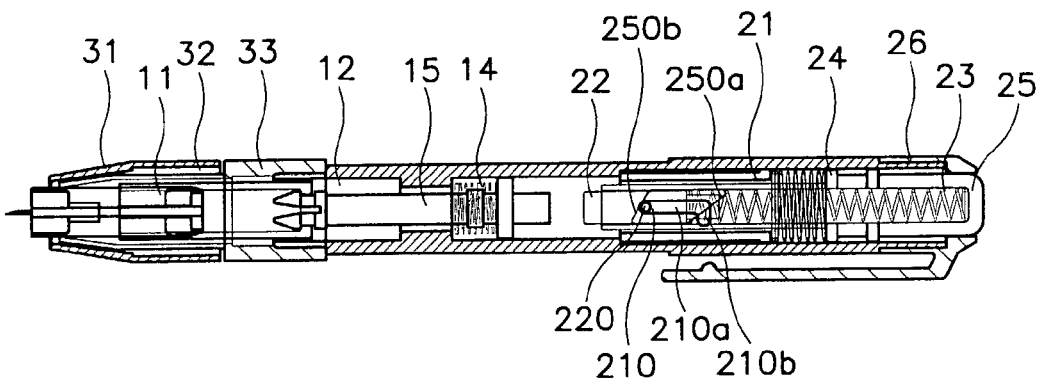

As shown in FIGS. 1 and 3, the impact-generating mechanism 20 has a pushing member 25 inserted and positioned at the back end of the body 13, and a back case 26 covering the pushing member 25 to prevent separation of the pushing member 25 from the body 13 and combined with the body 13. A first elastic member 23 for giving elasticity to an impact-transmitting member 22 is inserted into the hollow and cylindrical pushing member 25. The impact-transmitting member 22 is also inner-inserted into the pushing member 25 and positioned at the front of the first elastic member 23. The impact-transmitting member 22 has a penetration hole 221 penetrating across it, and an operating pin 220 is inserted in the penetration hole 221. Here, it is preferable that the length of the operating pin 220 is longer than that of the penetration hole 221, that is, diameter of the impact-transmitting member 22.

Pin-operating holes 250 are formed symmetrically on the cylindrical surface of the pushing member 25. Each of pin-operating holes 250 has a skew parallelogram shape.

A second elastic member 24 outer-inserted on the circumference of the pushing member 25 is contracted when the pushing member 25 is pushed, and elongated to return the pushing member 25 to the original position when the pushing force is removed.

A pin guide member 21 is fixed at a predetermined position within the body 13 and, is also outer-inserted onto the pushing member 25 and positioned at the front of the second elastic member 24. Therefore, the second elastic member 24 can be contracted with accumulating elasticity when a user pushes the pushing member 25, because it is supported at the back end of the pin guide member 21. Pin guide holes 210 is formed symmetrically on the circumference surface of the pin guide member 21 and each of them has a longitudinal path 210a and a circumferential path 210b. The both ends of the operating pin 220 inserted into the impact-transmitting member 22 are being bridged through the pin guide hole 210, and moved according to the path of the pin guide hole 210. When positioned at the circumferential path 210b of the pin guide hole 210, the longitudinal movement of the operating pin 220 is restrained (see (a) of FIG. 3).

Referring to (a) of FIG. 3, the impact-transmitting member 22 inner-inserted and the pin guide member 21 outer-inserted in the pushing member 25 are combined using the operating pin 220 penetrating the penetration hole 221. That is, the operating pin 220 penetrating the impact-transmitting member 22 passes through the pin-operating hole 250 formed on the pushing member 25 wrapping the outside of the impact-transmitting member 22. The operating pin 220 is then inserted in the pin guide hole 210 formed on the pin guide member 21 wrapping the pushing member 25. When the pushing member 25 is not pushed, the operating pin 220 is placed at the circumferential path 210b of the pin guide hole 210 on pin guide member 21.

Thereafter, when the pushing member 25 is pushed, the impact-transmitting member 22 cannot be moved according to the longitudinal direction (forward and backward) because the crooked hole 210 restrains the longitudinal movement of the operating pin 220. Since the pin guide member 21 is fixed at the body 13, the first and the second elastic members 23 and 24 are contracted and the pushing member 25 is only moved forwardly. As the push member 25 moves, the back sloping side 250a of the pin-operating hole 250 formed on the pushing member 25 presses the operating pin 220. Then, the operating pin 220 is moved according to the circumferential path 210b to the longitudinal path 210a of the pin guide hole 210 (see (b) of FIG. 3).

Thereafter, the contracted first elastic member is instantly elongated to the fore, and the operating pin 220 is moved forwardly according to the longitudinal path 220a together with the impact-transmitting member 22. Then, the impact-transmitting member 22 hits the impact-receiving member 15 (see (b) of FIG. 3). As a result, the lancet 11 combined with the front end of the impact-receiving member 15 is instantly ejected outwardly.

When the pressure of the pushing member 25 is removed, the contracted second elastic 24 is elongated, and moves the pushing member 25 to the back end. As the pushing member 25 is moved, the operating pin 220 is pressed by the front sloping surface 250b of the rising pin-operating hole 250. The operating pin 220 is then moved to the circumferential path 210b from the longitudinal path 210a, thereby the longitudinal movement is restrained.

Figure 4:
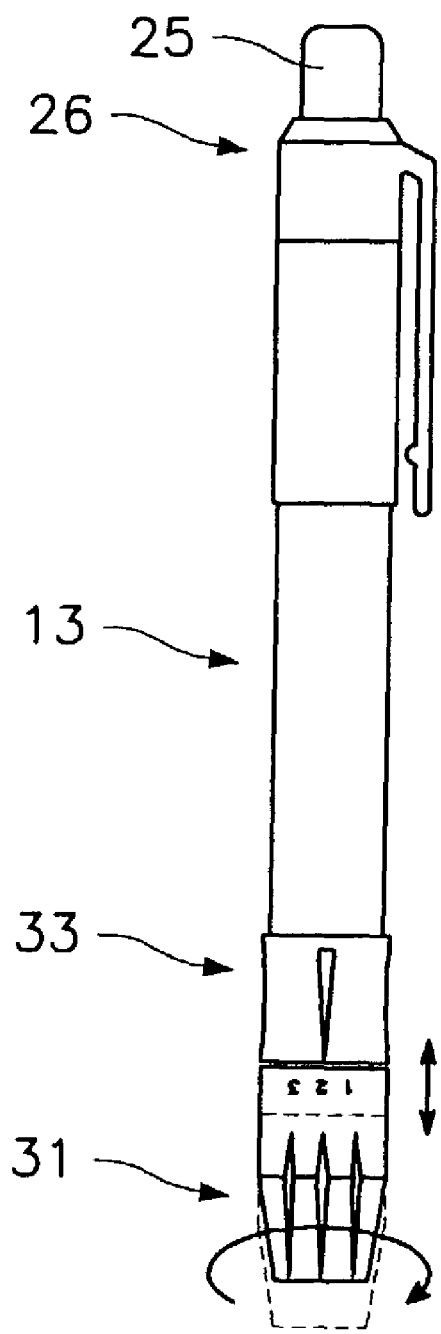
FIG. 4 is a assembly plane view of an automatic lancing device according to the present invention.
Figure 5:
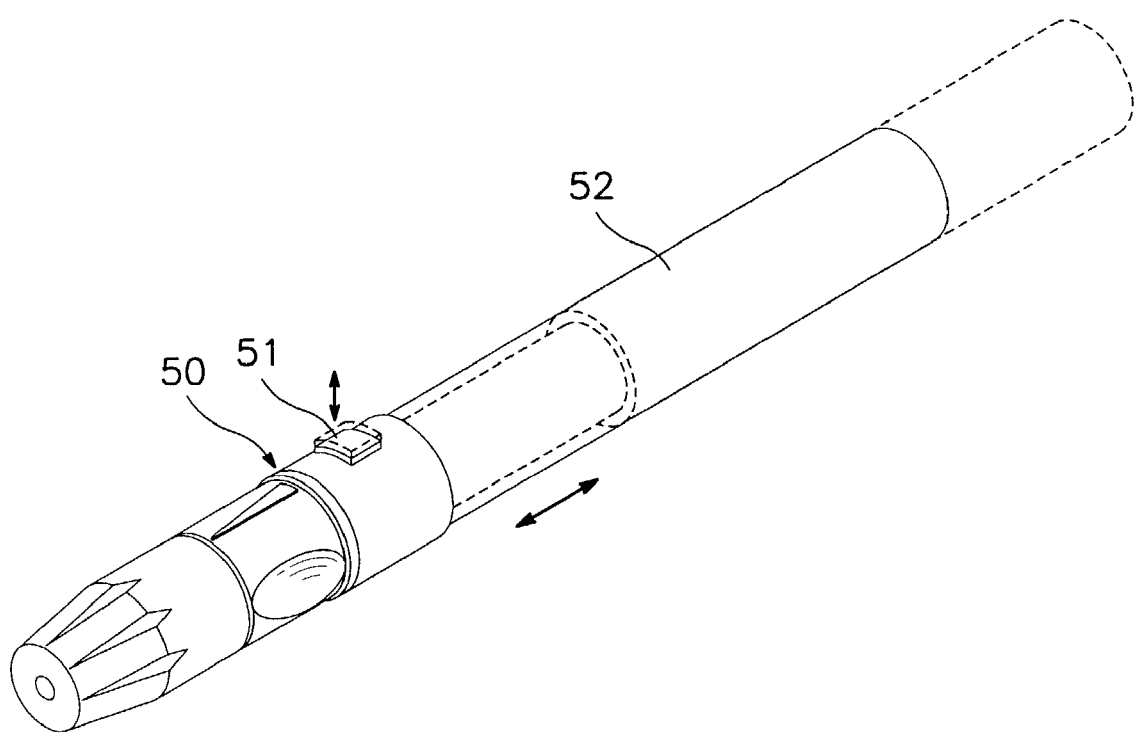
FIG. 5 is a perspective view of a conventional lancing device.

Referring to FIGS. 1 and 4, the length-regulating mechanism 30 is joined with the front end of the body 13 to cover the lancet 11 and the lancet holder 12. The length-regulating mechanism 30 has a front case 33 removably combined with the outer circumference of the body 13. As a result, the lancet 11 is easily exchanged by separating the front case 33 from the body 13 and removing the lancet 11 from the lancet holder 12. A helical thread 330 is formed on the outer circumference of the front case 33. A hollow cylindrical length-regulating member 32 having a protruding portion 320 for moving according to the thread 330 is combined with the front case 33. A cap 31 is fixed at the outer circumference of the length-regulating member 32, and encloses the length-regulating member 32. As shown in FIG. 4, when the cap 31 is rotated, the length-regulating member 32 rotates together according to the helical thread 330. As a result, when the cap 31 and the length-regulating member 32 are moved forwardly, the combination length between the cap 31 and the front case 33 is getting far and closes. As the combination length is changed, the length from the lancet 11 in the inside of the front case 33 to the leading end of the cap 31 increases or decreases. Therefore, the ejection length of the lancet 11 instantly ejected from the outside of the cap 31 by pushing the pushing member 25 can be regulated.

As discussed earlier, in the automatic lancing device of the present invention, the pushing member generating instant impact due to elasticity of the elastic member is positioned at the back end of the body, thereby preventing misoperation when a user happens to seize the body. The ejection length of the lancet can be regulated by rotating the cap and the length-regulating member combined with the front of the body. As a result, the automatic lancing device can be used at the skin having different thickness only by simply rotating the cap.

What is claimed is:

1. An automatic lancing device for withdrawing a blood sample, comprising:
   a hollow cylindrical body;
   an operation mechanism having a lancet exchangeably fitted at the front of a lancet holder positioned inside the body, and an impact-receiving member combined with the other side of the lancet holder and receiving impact to eject the lancet from the body;

an impact-generating mechanism having an impact-transmitting member positioned at a back end of the operation mechanism and transmitting impact to the impact-receiving member, wherein the impact-generating mechanism includes:

a pushing member being positioned at the back end of the body and having pin-operating holes which penetrate across it;

the impact-transmitting member having a penetrating hole and inner-inserted inside the pushing member, wherein a first elastic member is also inner-inserted inside the pushing member and interposed between the impact-transmitting member and the pushing member;

a pin guide member having pin guide holes penetrating across it and located outside the pushing member, wherein a second elastic member is also located outside the pushing member and interposed between the pin guide member and the pushing member; and an operating pin passing through the penetrating holes of the impact-transmitting member, the pin-operating holes of the pushing member and the pin-guide hole of the pin guide member and connecting these members;

wherein each of the pin guide holes has a circumferential path and a longitudinal path;

the operating pin located at the circumferential path is moved into the longitudinal path by the pin-operating hole when the pushing member is pushed; and the impact-transmitting member is moved forward with the operating pin according to the longitudinal path due to the first elastic member storing elasticity while the operating pin is being moved, and transmits impact into the impact-receiving member; and a length-regulating mechanism comprising a length-regulating member rotationably combined with the outer circumference of a front case enclosing the lancet at the front end of the body and regulating an ejection length of the lancet from the front case.

2. The automatic lancing device according to claim 1, wherein the front case has a helical thread at the outer circumference and the length-regulating member has a protruding portion for moving according to the helical thread.

* * * * *